United States Patent
Matsumura et al.

(10) Patent No.: US 10,093,968 B2
(45) Date of Patent: Oct. 9, 2018

(54) METHOD FOR IMPROVING NUCLEIC ACID SYNTHESIS REACTION

(71) Applicant: TAKARA BIO INC., Shiga (JP)

(72) Inventors: Kiyoyuki Matsumura, Shiga (JP); Takashi Uemori, Shiga (JP); Hiroyuki Mukai, Shiga (JP)

(73) Assignee: TAKARA BIO INC., Shiga (JP)

( * ) Notice: Subject to any disclaimer, the term of this patent is extended or adjusted under 35 U.S.C. 154(b) by 0 days.

(21) Appl. No.: 15/602,456

(22) Filed: May 23, 2017

(65) Prior Publication Data

US 2017/0260578 A1  Sep. 14, 2017

Related U.S. Application Data

(62) Division of application No. 14/372,558, filed as application No. PCT/JP2013/051490 on Jan. 24, 2013, now Pat. No. 9,689,013.

(30) Foreign Application Priority Data

Jan. 31, 2012 (JP) .................................. 2012-017665

(51) Int. Cl.
| | | |
|---|---|---|
| *C12Q 1/68* | (2018.01) | |
| *C12N 9/12* | (2006.01) | |
| *C12Q 1/6848* | (2018.01) | |
| *C12P 19/34* | (2006.01) | |
| *C12Q 1/6844* | (2018.01) | |

(52) U.S. Cl.
CPC ......... *C12Q 1/6848* (2013.01); *C12N 9/1252* (2013.01); *C12N 9/1276* (2013.01); *C12P 19/34* (2013.01); *C12Q 1/6844* (2013.01); *C12Y 207/07007* (2013.01)

(58) Field of Classification Search
CPC ... C12Q 1/6848; C12N 9/1252; C12N 9/1276
See application file for complete search history.

(56) References Cited

U.S. PATENT DOCUMENTS

| 6,300,075 B1 | 10/2001 | Preston et al. |
| 6,787,305 B1 | 9/2004 | Li |
| 2004/0248105 A1 | 12/2004 | Kumar |
| 2005/0069887 A1 | 3/2005 | Kitabayashi et al. |
| 2012/0329126 A1 | 12/2012 | Wang et al. |

FOREIGN PATENT DOCUMENTS

| EP | 1 930 422 | 6/2008 |
| JP | 2010-246528 | 11/2010 |
| JP | 2010-246529 | 11/2010 |
| WO | 99/46400 | 9/1999 |

OTHER PUBLICATIONS

International Preliminary Report on Patentability dated Aug. 5, 2014 in International (PCT) Application No. PCT/JP2013/051490.
Henke et al., "Betaine improves the PCR amplification of GC-rich DNA sequences", Nucleic Acids Research, 1997, vol. 25, No. 19, pp. 3957-3958.
Reeves et al., "The American Journal of Human Genetics", 1994, vol. 55, No. 3, p. 238, 1393.
International Search Report dated Apr. 9, 2013 in International (PCT) Application No. PCT/JP2013/051490.
WPINDEX data of JP 2010-246528 (Nov. 2010), AN 2010-N73275 and JP 2010-246529 (Nov. 2010), AN 2010-N73273, copyright 2014.
Extended European Search Report dated Nov. 20, 2015 in corresponding European Application No. 13743868.5.
Kondakova et al., "Effect of low-molecular amines on DNA conformation and stability of the double helix", Database Medline, US National Library of Medicine, XP-002750391, Sep. 1975, 1 page.
Kondakova et al., "Effect of low-molecular amines on the conformation and stability of the DNA double helix", Molekulyarnaya Biologiya, vol. 9, No. 5, Sep. 1975, pp. 593-596.
Communication pursuant to Article 94(3) EPC dated Oct. 5, 2017 in European Application No. 13 743 868.5.

*Primary Examiner* — David C Thomas
(74) *Attorney, Agent, or Firm* — Wenderoth, Lind & Ponack, L.L.P.

(57) ABSTRACT

Provided are the following: a method, for improving reactivity of an acid synthesis reaction, comprising a step for adding an ω-amino acid to a reaction solution; a composition, for a nucleic acid synthesis reaction, comprising DNA polymerase, reaction buffer, at least one primer, at least one deoxyribonucleoside triphosphate, and an ω-amino acid; and a reaction buffer, for a nucleic acid synthesis reaction, comprising an ω-amino acid.

5 Claims, 3 Drawing Sheets

Specification includes a Sequence Listing.

[Figure 1]
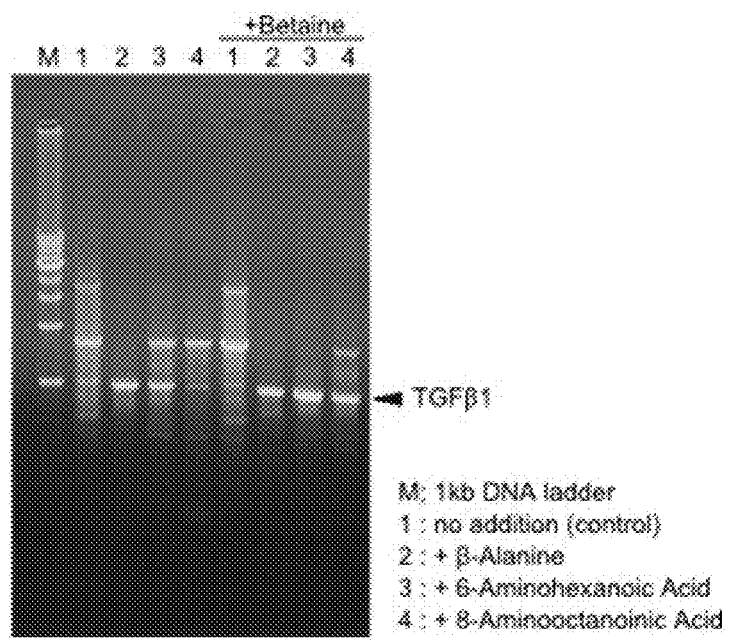
[Figure 2]
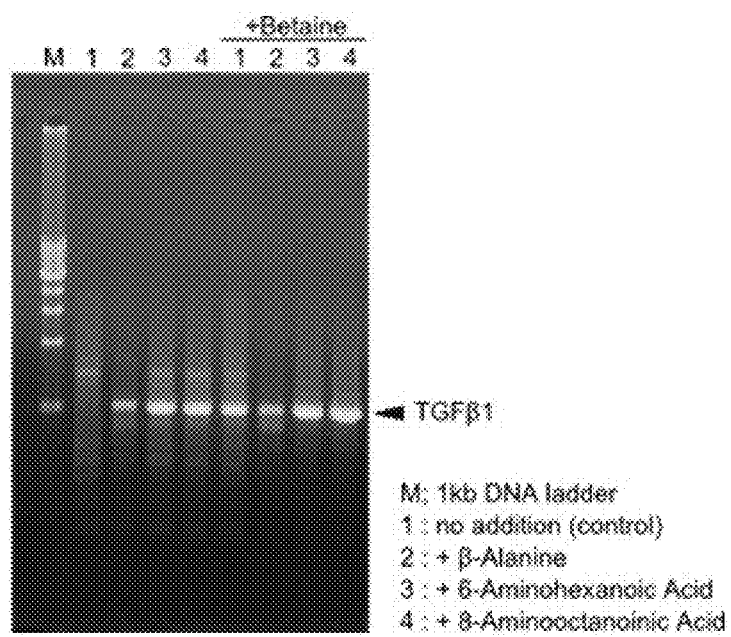

[Figure 3]
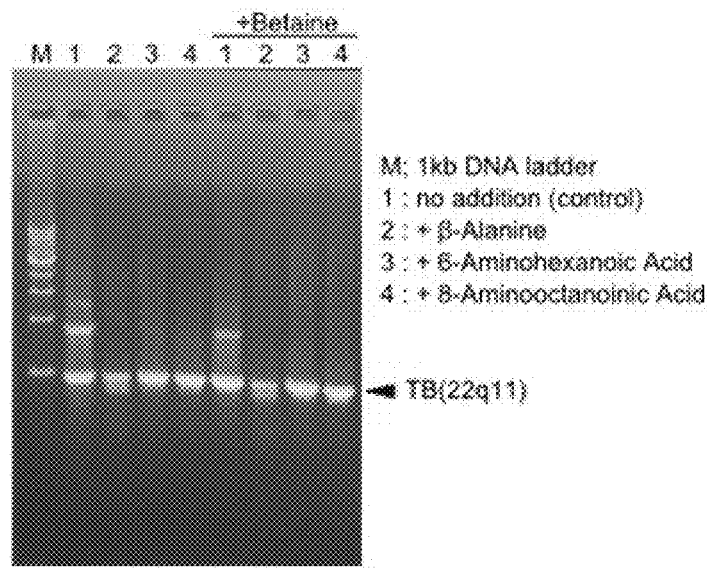
[Figure 4]
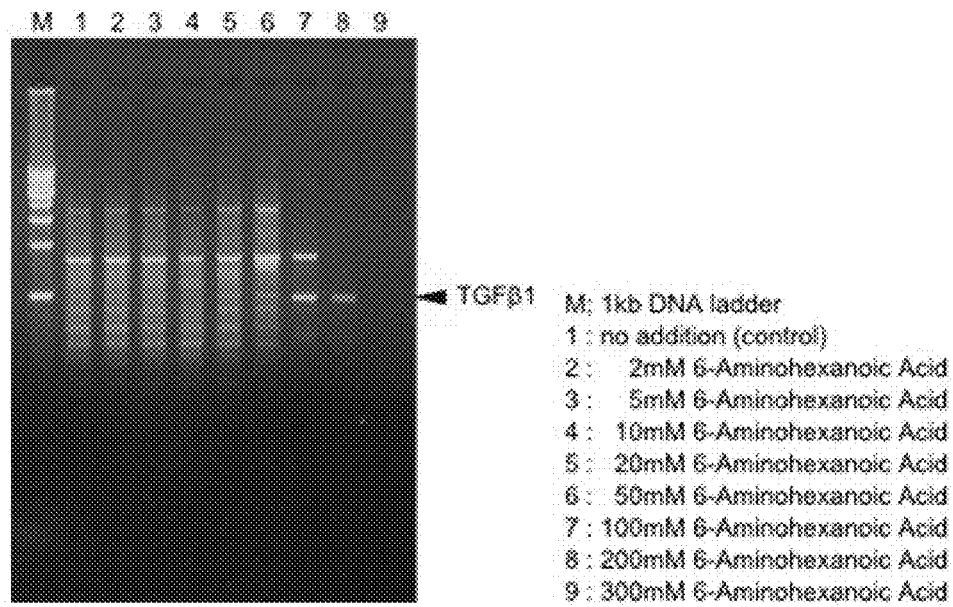

[Figure 5]
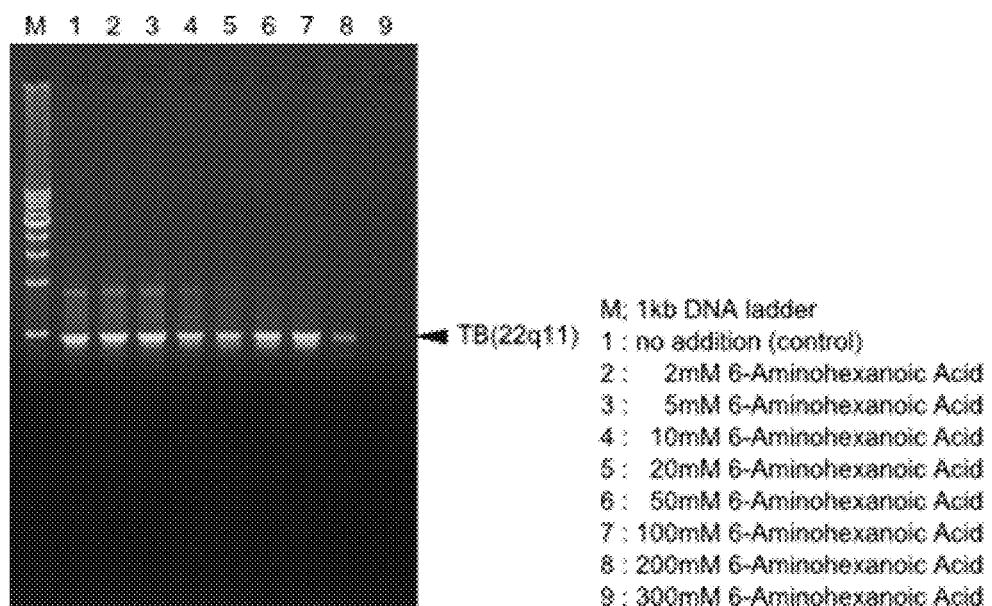

METHOD FOR IMPROVING NUCLEIC ACID SYNTHESIS REACTION

TECHNICAL FIELD

The present invention relates to a method for improving reactivity of a nucleic acid synthesis reaction, a composition for a nucleic acid synthesis reaction, and a reaction buffer for a nucleic acid synthesis reaction.

BACKGROUND ART

A nucleic acid synthesis method, in particular a polymerase chain reaction (PCR) method, is a technique for simply amplifying a nucleic acid fragment of interest in a test tube, and recently becomes an essential experimental means not only for genetic research but also in a wide variety of fields in biology, medicine, and agriculture.

A nucleic acid synthesis reaction using a DNA polymerase such as PCR often has a problem with its reactivity such as specificity. In order to avoid a non-specific nucleic acid synthesis reaction, development of novel DNA polymerases, improvement of primer design methods, optimization of reaction solution composition, addition of compounds, and the like are attempted. For example, addition of betaine is found to be effective in amplifying CG-rich templates (Nonpatent Literatures 1 and 2).

CITATION LIST

Nonpatent Literature

Nonpatent Literature 1: "American Journal of Human Genetics", Sep. 1, 1994, Vol.55, Supplement No.3, p. A238

Nonpatent Literature 2: "Nucleic Acids Research", Oct. 1, 1997, Vol.25, No.19, p. 3957-3958

SUMMARY OF INVENTION

Problems to be Solved by the Invention

There have been attempts to improve reactivity of a nucleic acid synthesis reaction. However, a nucleic acid synthesis reaction may be still accompanied by a nonspecific reaction or may not synthesize an enough amount of DNA. For these reasons, further improvement in reactivity of a nucleic acid synthesis reaction is needed. An object of the present invention is to provide a method for improving reactivity of a nucleic acid synthesis reaction, a composition for a nucleic acid synthesis reaction, and a reaction buffer for a nucleic acid synthesis reaction.

Solution to Problems

The present inventors found that reactivity of a nucleic acid synthesis reaction could be improved by addition of an ω-amino acid to a reaction solution. Thus, the present invention was completed.

That is, the present invention relates to:

[1] A method for improving reactivity of a nucleic acid synthesis reaction, comprising a step of adding an ω-amino acid to a reaction solution;

[2] The method according to [1], wherein the ω-amino acid is a compound represented by the following formula 1:

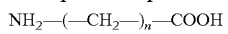
NH$_2$—(—CH$_2$—)$_n$—COOH    [Chemical formula 1]

wherein n is an integer of 2 or more;

[3] The method according to [2], wherein n is an integer of 2 to 7;

[4] The method according to [1], wherein the nucleic acid synthesis reaction is a polymerase chain reaction;

[5] The method according to [1], comprising a step of preparing a reaction solution containing an ω-amino acid, a DNA polymerase, at least one primer, and at least one deoxyribonucleoside triphosphate;

[6] The method according to [1], further comprising a step of adding betaine to the reaction solution;

[7] A composition for a nucleic acid synthesis reaction, containing: a DNA polymerase, a reaction buffering agent, at least one primer, at least one deoxyribonucleoside triphosphate, and an ω-amino acid;

[8] The composition according to [7], wherein the ω-amino acid is a compound represented by the formula 1 as defined in [2];

[9] The composition according to [7], further containing betaine;

[10] A reaction buffer for a nucleic acid synthesis reaction, containing an ω-amino acid;

[11] The reaction buffer according to [10], wherein the ω-amino acid is a compound represented by the formula 1 as defined in [2];

[12] The reaction buffer according to [10], further containing betaine;

[13] A kit for a nucleic acid synthesis reaction, comprising the following components:
a DNA polymerase,
a reaction buffering agent,
at least one deoxyribonucleoside triphosphate, and
an ω-amino acid;

[14] The kit according to [13], wherein the ω-amino acid is a compound represented by the formula 1 as defined in [2];

[15] The kit according to [13], further comprising betaine.

Effects of the Invention

According to the present invention, a method for improving reactivity of a nucleic acid synthesis reaction, a composition for a nucleic acid synthesis reaction which has excellent reactivity, and a reaction buffer for a nucleic acid synthesis reaction are provided.

BRIEF DESCRIPTION OF DRAWINGS

FIG. 1 shows a result of agarose gel electrophoresis in Example 1.

FIG. 2 shows a result of agarose gel electrophoresis in Example 2.

FIG. 3 shows a result of agarose gel electrophoresis in Example 3.

FIG. 4 shows a result of agarose gel electrophoresis in Example 4.

FIG. 5 shows a result of agarose gel electrophoresis in Example 5.

MODE FOR CARRYING OUT THE INVENTION

The method for improving reactivity of a nucleic acid synthesis reaction of the present invention comprises a step of adding an ω-amino acid to a reaction solution. When a nucleic acid synthesis reaction is carried out using a DNA polymerase in a reaction solution containing an ω-amino acid, the reactivity of the nucleic acid synthesis reaction can be improved. The present invention also provides a nucleic acid synthesis method with excellent reactivity.

The nucleic acid synthesis reaction in the method of the present invention is not particularly limited as long as it is a reaction for synthesizing a DNA complementary to a DNA or RNA template. Examples of the nucleic acid synthesis reaction are nucleic acid synthesis reactions well known in the art, including a primer extension reaction, a reverse transcription reaction, PCR, a reverse transcription polymerase chain reaction (RT-PCR), an ICAN method, a LAMP method, and an SDA method.

When the present invention is used for improvement in reactivity of PCR, general conditions are applicable to thermal cycling conditions for the PCR. For example, PCR is carried out by a reaction consisting of three steps: melting (denaturation) of a double stranded DNA template into single strands, annealing of primers to the single stranded DNA templates, and synthesis (extension) of complementary strands from the primers, or by a two-step reaction, called "shuttle PCR" [see "PCR method-Forefront (SaiZenSen)", Extra issue of "Protein, Nucleic Acid, and Enzyme", Vol.41, No.5, p. 425-428 (1996)], wherein the annealing step and the extension step of the above-described three-step reaction are carried out at the same temperature.

As used herein, the improvement in reactivity of a nucleic acid synthesis reaction means, for example, an effect selected from the group consisting of an improvement in reaction specificity and an increase in the synthesis amount of a DNA having a target nucleotide sequence, but which the present invention is not limited to. According to the present invention, the reactivity of a nucleic acid synthesis reaction can be improved by addition of an ω-amino acid to a reaction solution. When deduced from the improving effect of ω-amino acids on the reactivity of a nucleic acid synthesis reaction which has been shown by the present invention, ω-amino acids possibly have an ability to improve the priming specificity of primers, but which the present invention is not limited to. The improvement in reactivity of a nucleic acid synthesis reaction by an ω-amino acid can be confirmed by, for example, carrying out a nucleic acid synthesis reaction with a reaction solution containing an ω-amino acid and a nucleic acid synthesis reaction with a reaction solution containing no ω-amino acid, subjecting the reaction solutions obtained after the reactions to agarose gel electrophoresis, and then comparing the reaction specificity or the synthesis amount of a DNA having a target nucleotide sequence between the nucleic acid synthesis reactions. The improvement in reactivity of a nucleic acid synthesis reaction by an ω-amino acid can also be confirmed by monitoring amplification of a nucleic acid using an intercalating dye, a FRET (Fluorescence Resonance Energy Transfer) labeled probe or the like, and then comparing the reaction specificity or the synthesis amount of a DNA having a target nucleotide sequence between a nucleic acid synthesis reaction with a reaction solution containing an ω-amino acid and a nucleic acid synthesis reaction with a reaction solution containing no ω-amino acid. Improvement in the reaction specificity as described above is evaluated, for example, based on a reduction in frequency of non-specific nucleic acid amplification or a reduction in the synthesis amount of the non-specifically amplified nucleic acid.

As used herein, amino acids are interpreted in a broad sense and also include amino acids comprising a sulfo group in place of a carboxyl group. As used herein, the ω-amino acid means an amino acid having a primary amino group bound to a terminal carbon on the side opposite to the carbon to which a carboxyl group or a sulfo group is bound, and excluding α-amino acids. As used herein, the ω-amino acid also includes a β-amino acid, a γ-amino acid, a δ-amino acid, and an ε-amino acid. Examples of the ω-amino acid that can be used in the present invention include, but not limited to, ω-amino acids containing 3 or more carbon atoms, and preferably ω-amino acids containing 3 to 8 carbon atoms. Examples of such an ω-amino acid include compounds represented by the following formula 1:

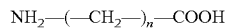  [Chemical formula 2]

wherein n is an integer of 2 or more. Among such compounds, preferred are compounds represented by the formula 1 wherein n is an integer of 2 to 7.

Examples of the ω-amino acid represented by the formula 1 include β-alanine, γ-amino-n-butyric acid (GABA), δ-aminopentanoic acid (5-aminopentanoic acid), ε-aminohexanoic acid (6-aminohexanoic acid), ω-aminoheptanoic acid (7-aminoenanthic acid), and 8-aminooctanoic acid, 9-aminononanoic acid, and 10-aminodecanoic acid.

In the method of the present invention, the ω-amino acid is added to a reaction solution in an amount effective for improving reactivity of a nucleic acid synthesis reaction by a DNA polymerase. The concentration of the ω-amino acid in a reaction solution which is expected to improve reactivity of a nucleic acid synthesis reaction can be easily determined by, for example, the above-described method for confirming improvement in reactivity of a nucleic acid synthesis reaction. For example, when 6-aminohexanoic acid is used as the ω-amino acid in the method of the present invention, the concentration of 6-aminohexanoic acid in a reaction solution is preferably less than 300 mM, more preferably 10 to 200 mM, and still more preferably 20 to 200 mM, for example 100 mM, but which the present invention is not limited to. When β-alanine is used as the ω-amino acid in the method of the present invention, the concentration of β-alanine in a reaction solution is preferably 1 M or less, more preferably 100 to 500 mM, and still more preferably 250 to 500 mM, for example 500 mM. The suitable concentration range of the ω-amino acid in a reaction solution can be easily determined depending on the kind of a DNA polymerase to be used, the target sequence and the like, for example, in the same manner as Example 4 or Example 5 as described later.

The reaction solution for a nucleic acid synthesis reaction in the method of the present invention can be prepared from a combination of compositions containing an ω-amino acid, a DNA polymerase, a reaction buffering agent, at least one primer, at least one deoxyribonucleoside, and a nucleic acid as a template, and the like. As an aspect of the present invention, provided is a composition containing a DNA polymerase, a reaction buffering agent, at least one primer, at least one deoxyribonucleoside, and an ω-amino acid. As another aspect of the present invention, provided is a kit containing a DNA polymerase, a reaction buffering agent, at least one deoxyribonucleoside triphosphate, and an ω-amino acid. The kit may contain one or more primers.

The DNA polymerase that can be used in the present invention may be any kind of DNA polymerase as long as it has the ability to synthesize a DNA complementary to a DNA or RNA template. The DNA polymerase that can be used in the present invention is preferably a heat-stable DNA-directed DNA polymerase. Examples of such a DNA polymerase include heat-stable DNA polymerases derived from bacteria, such as DNA polymerases derived from bacteria of the genus *Thermus* (DNA polymerases derived from *Thermus aquaticus*, etc.) and DNA polymerases derived from thermophilic bacteria of the genus *Bacillus*

(DNA polymerases derived from *Bacilus caldotenax*, etc.), and DNA polymerases derived from archaea such as DNA polymerases derived from archaea of the genus *Pyrococcus* (DNA polymerases derived from *Pyrococcus* sp., etc.) and DNA polymerases derived from archaea of the genus *Thermococcus* (DNA polymerases derived from *Thermococcus Kodakaraensis*).

As the DNA polymerase, two or more kinds of DNA polymerases may be used in combination. Examples of two or more kinds of DNA polymerases include combinations of DNA polymerases having 3'→5' exonuclease activity and DNA polymerases that do not substantially have 3'→5' exonuclease activity. A technique for PCR with a reaction solution containing such two kinds of DNA polymerases is known as LA-PCR (Long and Accurate PCR).

The amount used of the DNA polymerase in the method of the present invention is not particularly limited, and for example, it may be an amount used for a conventional nucleic acid synthesis reaction. For PCR, the amount used of a suitable DNA polymerase is well known to a person skilled in the art. For example, when a DNA synthesis reaction is carried out in 25 μl of a reaction solution using a DNA polymerase from Thermus aquaticus, the amount of the enzyme contained in the reaction solution is 0.125 U to 5 U.

The reaction buffering agent as used herein means a compound or a mixture having an ability to reduce changes in the hydrogen-ion concentration (pH) of a reaction solution. A mixture solution of a weak acid and a salt thereof or a weak base and a salt thereof is widely used as a reaction buffering agent for the purpose of controlling pH, because the mixture solution generally has a strong buffering action. In the present invention, various reaction buffering agents known in the field of biochemistry can be used. Examples of the reaction buffering agent include good buffers such as Tris hydrochloric acid, Tris acetic acid, HEPES potassium hydroxide, and HEPES sodium hydroxide, and phosphate buffers. The pH of the reaction solution in the method of the present invention is suitably set in the usual range within which a gene amplification reaction is carried out, for example, in the range of pH 8.0-9.5 at 25° C.

The primer is an oligonucleotide having a nucleotide sequence complementary to a template nucleic acid. The primer is not particularly limited as long as it is annealed to the template nucleic acid under the reaction conditions used. When the present invention is used for PCR, two or more primers that can amplify a target sequence and are oriented oppositely to each other may be designed and used. The primer length is preferably 6 nucleotides or more, more preferably 10 nucleotides or more from the viewpoint of specific annealing, and preferably 100 nucleotides or less, more preferably 30 nucleotides or less from the viewpoint of oligonucleotide synthesis. The oligonucleotide may be chemically synthesized, for example, by a known method. The oligonucleotide may also be an oligonucleotide derived from a biological sample. For example, the oligonucleotide may be prepared by isolation from a digestion product of a DNA prepared from a natural sample with a restriction endonuclease.

The deoxyribonucleoside is a compound in which deoxyribose is bonded to an organic base and a phosphate group is bonded to the deoxyribose via phosphoester linkage. Four kinds of deoxyribonucleosides which have adenine, guanine, cytosine and thymine bases respectively are found in natural DNAs. The adenine, guanine, cytosine and thymine bases are often abbreviated to A, G, C and T respectively. The deoxyribonucleoside includes a free monophosphate type, a diphosphate type and a triphosphate type (i.e., in which the phosphate group is composed of one, two or three phosphate moieties). It is known that a deoxyribonucleoside triphosphate having hypoxanthine or uracil as the base can also be used for a nucleic acid synthesis reaction. In the present invention, at least one of deoxyribonucleoside triphosphates (e.g., dATP, dCTP, dITP, dGTP and dTTP) and their derivatives is used. A preferred example of the deoxyribonucleoside triphosphate contained in the composition of the present invention includes a mixture of four kinds of deoxyribonucleoside triphosphates, i.e. a mixture of dATP, dCTP, dGTP and dTTP.

In the method of the present invention, the step of adding an ω-amino acid to a reaction solution may be carried out at any stage during preparation of the reaction solution. The step of adding an ω-amino acid to a reaction solution is preferably carried out before incubation of the reaction solution at a suitable temperature for a nucleic acid synthesis reaction. For example, a nucleic acid synthesis reaction may be carried out after a solution containing a reaction buffering agent (a reaction buffer) to which an ω-amino acid is previously added is combined with a DNA polymerase, at least one primer, at least one deoxyribonucleoside triphosphate and a template nucleic acid to prepare a reaction solution.

Accordingly, the reaction buffer containing an ω-amino acid for a nucleic acid synthesis reaction is a preferred aspect of the present invention. The reaction buffer may further contain a bivalent cation and/or a monovalent cation, or a salt thereof, and other components useful for a nucleic acid synthesis reaction, in addition to the ω-amino acid and the reaction buffering agent. Preferred examples of the bivalent cation include bivalent metal ions such as a magnesium ion and a manganese ion. Preferred examples of the monovalent cation include a sodium ion, a potassium ion, and an ammonium ion. Preferred examples of the other components useful for a nucleic acid synthesis reaction include anionic surfactants, nonionic surfactants, and tetramethylammonium salts.

The method of the present invention may further comprise a step of adding betaine to the reaction solution. The step of adding betaine to the reaction solution may be carried out at any stage during preparation of the reaction solution. The step of adding betaine to the reaction solution is preferably carried out before incubation of the reaction solution at a suitable temperature for a nucleic acid synthesis reaction. The composition of the present invention and the reaction buffer of the present invention may also contain betaine. The betaine as used herein collectively means compounds having a positive charge and a negative charge at positions that are not adjacent to each other in the same molecule, in which a dissociable hydrogen atom is not bound to the atom with the positive charge, and having no charge as the whole molecule. Representative examples of betaine include trimethylglycine and derivatives thereof.

Betaine is known as an additive capable of increasing the reactivity of a nucleic acid synthesis reaction. The present inventors have found that an ω-amino acid and betaine produce a synergistic effect on the reactivity of a nucleic acid synthesis reaction. Although a nucleic acid amplification reaction may be inhibited by addition of an ω-amino acid at a high concentration, the present inventors have observed that the inhibition of a nucleic acid amplification reaction is removed by addition of betaine. The addition amount of betaine in the method of the present invention is not particularly limited as long as it is in such a range that an increase in the reactivity of a nucleic acid synthesis reaction by betaine is found, and it is preferably 0.1 M to 3 M, more preferably 0.3 M to 2.5 M.

The present invention can also be used for real-time PCR in which amplification of a nucleic acid can be monitored using an intercalating dye, a FRET labeled probe, or the like. In such a case, the reaction solution in the method of the present invention, the composition of the present invention, and the reaction buffer of the present invention may contain an intercalating dye, or a FRET labeled probe.

EXAMPLES

Hereinafter, the present invention is more specifically explained by reference to Examples which the present invention is not limited to. In the following Examples, TaKaRa PCR Thermal Cycler Dice (registered trademark) Gradient (manufactured by TAKARA BIO INC.) was used as a reaction device for PCR.

Example 1

After β-alanine (manufactured by SIGMA-ALDRICH) was dissolved in ultrapure water (Milli-Q water), Tris acetate buffer (pH 8.9) was added dropwise to prepare a 5 M β-alanine solution of pH 8.5. In the same manner, after 6-aminohexanoic acid (manufactured by SIGMA-ALDRICH) was dissolved in ultrapure water (Milli-Q water), the pH of the solution was adjusted to prepare a 2 M 6-aminohexanoic acid solution of pH 8.5, and after 8-aminooctanoic acid (manufactured by SIGMA-ALDRICH) was dissolved in ultrapure water (Milli-Q water), the pH of the solution was adjusted to prepare a 1 M 8-aminooctanoic acid solution of pH 8.5. Betaine (trimethylglycine; B2629, manufactured by SIGMA-ALDRICH) was dissolved in ultrapure water (Milli-Q water) to prepare a 5 M betaine solution. These were used in preparation of reaction solutions described below.

PCR reaction solutions for amplification of 987 bp (GC rate: 72.3%) of a TGF β1 gene region were prepared on ice using TaKaRa Ex Taq (registered trademark) Hot Start Version (manufactured by TAKARA BIO INC.), 100 ng of Human genomic DNA (manufactured by Clontech Laboratories Inc.) as a template, and a primer consisting of a base sequence shown in SEQ ID NO:1 and a primer consisting of a base sequence shown in SEQ ID NO:2 as a primer pair. Four kinds of PCR reaction solutions in total were prepared which have the reaction solution composition described in the attached instruction of the commercial product, and each of which was 20 µL of a reaction solution additionally containing β-alanine at a final concentration of 500 mM, 6-aminohexanoic acid at a final concentration of 100 mM or 8-aminooctanoic acid at a final concentration of 50 mM as the ω-amino acid, or 20 µL of a reaction solution containing no ω-amino acid as a control. Furthermore, to the composition of the reaction solutions thus obtained was added betaine (trimethylglycine) to prepare additional four kinds of reaction solutions containing betaine at a final concentration of 300 mM. Next, the PCR reaction solutions thus prepared on ice were subjected to PCR consisting of an activation reaction at 94° C. for 1 minute and then 35 cycles with each cycle consisting of 98° C. for 10 seconds, 55° C. for 30 seconds and 72° C. for 1 minute. After completion of PCR, 4 µL of each reaction solution was subjected to agarose gel electrophoresis to confirm the chain length and amplification amount of an amplified product. A result of the agarose gel electrophoresis is shown in FIG. 1. In FIG. 1, M shows a lane in which 200 ng of 1 kb DNA Ladder (manufactured by TAKARA BIO INC.) marker was loaded.

As a result, when the PCR reaction solution contained no ω-amino acid, a band corresponding to the desired amplified product of 987 bp was hardly detected. In contrast, when the PCR reaction solution contained any ω-amino acid, a band corresponding to the desired amplified product of 987 bp was detected. When the PCR reaction solution contained betaine in addition to the ω-amino acid, the amplification amount of the desired amplified product of 987 bp was increased. When the PCR reaction solution contained β-alanine or the PCR reaction solution contained 6-aminohexanoic acid and betaine, specific amplification of the desired amplified product of 987 bp was detected.

Example 2

The effect of ω-amino acid was examined in the same manner as Example 1 except that Pyrobest (registered trademark) DNA Polymerase (manufactured by TAKARA BIO INC.) was used instead of TaKaRa Ex Taq (registered trademark) (manufactured by TAKARA BIO INC.) and the final concentration of betaine in the PCR reaction solutions containing betaine was adjusted to 1 M. Pyrobest (registered trademark) DNA Polymerase is a commercial product containing a DNA polymerase derived from *Pyrococcus* sp.

After completion of PCR, 4 µL of each reaction solution was subjected to agarose gel electrophoresis. A result is shown in FIG. 2. In FIG. 2, M shows a lane in which 200 ng of 1 kb DNA Ladder (manufactured by TAKARA BIO INC.) marker was loaded. As a result, when the PCR reaction solution contained no ω-amino acid and no betaine, only non-specific amplified products were detected. In contrast, when the PCR reaction solution contained the ω-amino acid, the desired product of 987 bp was detected as the main amplified product, and in addition, an increase of the amplification amount was also confirmed. When the PCR reaction solution contained betaine in addition to the ω-amino acid, non-specific amplification was hardly observed and the desired product of 987 bp was specifically amplified. When the PCR reaction solution contained β-alanine or the PCR reaction solution contained 6-aminohexanoic acid and betaine, the amplified amount of the desired product of 987 bp was increased as compared with the PCR reaction solution containing only betaine.

Example 3

The effect of ω-amino acid was confirmed in the same manner as Example 1 except that a primer pair (a primer consisting of a base sequence shown in SEQ ID NO:3 and a primer consisting of a base sequence shown in SEQ ID NO:4) for amplifying 965 bp (GC rate: 35.4%) of a Homo sapiens DNA, translocation breakpoint sequences on 22q11: Type C (GenBank: AB261999.1) region was used instead of the primer pair for amplifying the TGF β1 gene region.

After completion of PCR, 4 µL of each reaction solution was subjected to agarose gel electrophoresis. A result is shown in FIG. 3. In FIG. 3, M shows a lane in which 200 ng of 1 kb DNA Ladder (manufactured by TAKARA BIO INC.) marker was loaded. As a result, when the PCR reaction solution contained no ω-amino acid, non-specific amplification was observed in addition to amplification of the desired product. In contrast, when the PCR reaction solution contained any ω-amino acid, the non-specific amplification was suppressed.

From the above-described results, it was shown that the addition of an ω-amino acid to a PCR reaction solution was effective not only for amplification of a template DNA having a high GC rate, but also for amplification of a template DNA having a low GC rate (a high AT rate) which is difficult to amplify.

Example 4

The concentration of 6-aminohexanoic acid which was effective for improvement in reactivity of a nucleic acid synthesis reaction was examined. Nine kinds of reaction solutions in total were prepared, which are the same reaction solutions as those of Example 1 except that they contained 6-aminohexanoic acid at a final concentration of 2 mM, 5 mM, 10 mM, 20 mM, 50 mM, 100 mM, 200 mM or 300 mM instead of the various ω-amino acids, and 20 μL of a reaction solution containing no ω-amino acid as a control. Next, PCR was carried out in the same manner as Example 1, and then 4 μL of each reaction solution was subjected to agarose gel electrophoresis to confirm the chain length and amplification amount of an amplified product. A result of the agarose gel electrophoresis is shown in FIG. 4. In FIG. 4, M shows a lane in which 200 ng of 1 kb DNA Ladder (manufactured by TAKARA BIO INC.) marker was loaded.

As a result, when 6-aminohexanoic acid was added at 20 mM or more, a band probably corresponding to the desired amplified DNA was observed. When 6-aminohexanoic acid was added at 200 mM, only the desired DNA was amplified.

Example 5

The effective concentration of 6-aminohexanoic acid which was effective for improvement in reactivity of a nucleic acid synthesis reaction was examined in the same manner as Example 4 except that a primer pair (a primer consisting of a base sequence shown in SEQ ID NO:3 and a primer consisting of a base sequence shown in SEQ ID NO:4) for a Homo sapiens DNA, translocation breakpoint sequences on 22q11: Type C (GenBank: AB261999.1) region was used instead of the primer pair for amplifying the TGF β1 gene region.

After completion of PCR, 4 μL of each reaction solution was subjected to agarose gel electrophoresis. A result is shown in FIG. 5. In FIG. 5, M shows a lane in which 200 ng of 1 kb DNA Ladder (manufactured by TAKARA BIO INC.) marker was loaded. As a result, when 6-aminohexanoic acid was added at 10 mM or more, a band probably corresponding to the desired amplified DNA was observed. When 6-aminohexanoic acid was added at 50 mM, 100 mM or 200 mM, only the desired DNA was amplified.

INDUSTRIAL APPLICABILITY

The present invention is useful in a wide variety of fields including gene technology, biology, medicine, and agriculture.

Sequence Listing Free Text

SEQ ID NO:1; Synthetic primer for PCR to amplify of TGF-beta 1 gene.

SEQ ID NO:2; Synthetic primer for PCR to amplify of TGF-beta 1 gene.

SEQ ID NO:3; Synthetic primer for PCR to amplify of translocation breakpoint sequence region.

SEQ ID NO:4; Synthetic primer for PCR to amplify of translocation breakpoint sequence region.

The invention claimed is:

1. A composition for a nucleic acid synthesis reaction, containing:
   a DNA polymerase,
   a reaction buffering agent,
   at least one primer,
   at least one deoxyribonucleoside triphosphate, and
   an ω-amino acid
   wherein the ω-amino acid is selected from the group consisting of β-alanine, δ-aminopentanoic acid (5-aminopentanoic acid), ε-aminohexanoic acid (6-aminohexanoic acid), ω-aminoheptanoic acid (7-aminoenanthic acid), 8-aminooctanoic acid, 9-aminononanoic acid, and 10-aminodecanoic acid.

2. The composition according to claim 1, further containing betaine.

3. A reaction buffer for a nucleic acid synthesis reaction, containing
   betaine, and
   an ω-amino acid
   wherein the ω-amino acid is selected from the group consisting of β-alanine, δ-aminopentanoic acid (5-aminopentanoic acid), ε-aminohexanoic acid (6-aminohexanoic acid), ω-aminoheptanoic acid (7-aminoenanthic acid), 8-aminooctanoic acid, 9-aminononanoic acid, and 10-aminodecanoic acid.

4. A kit for a nucleic acid synthesis reaction, comprising the following components:
   a DNA polymerase,
   a reaction buffering agent,
   at least one deoxyribonucleoside triphosphate, and
   an ω-amino acid
   wherein the ω-amino acid is selected from the group consisting of β-alanine, δ-aminopentanoic acid (5-aminopentanoic acid), ε-aminohexanoic acid (6-aminohexanoic acid), ω-aminoheptanoic acid (7-aminoenanthic acid), 8-aminooctanoic acid, 9-aminononanoic acid, and 10-aminodecanoic acid.

5. The kit according to claim 4, further comprising betaine.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic primer for PCR to amplify of TGF-beta
      1 gene.

<400> SEQUENCE: 1
aggaggcagc accctgtttg                                                      20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer for PCR to amplify of TGF-beta
      1 gene.

<400> SEQUENCE: 2
tcgagggaaa gctgaggtcc                                                      20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer for PCR to amplify of
      translocation breakpoint sequence region.
```

```
<400> SEQUENCE: 3
gtgccagaac caggaatgaa                                              20

<210> SEQ ID NO 4
<211> LENGTH: 21
<212> TYPE: DNA
<213> ORGANISM: Artificial Sequence
<220> FEATURE:
<223> OTHER INFORMATION: Synthetic primer for PCR to amplify of
      translocation breakpoint sequence region.

<400> SEQUENCE: 4
ggaatgactt gaggccactg a                                            21
```